(12) United States Patent
Morgan et al.

(10) Patent No.: US 6,280,992 B1
(45) Date of Patent: Aug. 28, 2001

(54) **TYPE II RESTRICTION ENDONUCLEASE, HPY99I, OBTAINABLE FROM *HELICOBACTER PYLORI* J99 AND A PROCESS FOR PRODUCING THE SAME**

(75) Inventors: Richard D. Morgan, Middleton, MA (US); Qing Xu, Nashville, TN (US)

(73) Assignees: New England Biolabs, Inc., Beverly, MA (US); Vanderbilt University, Nashville, TN (US)

( * ) Notice: Subject to any disclaimer, the term of this patent is extended or adjusted under 35 U.S.C. 154(b) by 0 days.

(21) Appl. No.: 09/404,056

(22) Filed: Sep. 23, 1999

(51) Int. Cl.$^7$ .................................................... C12N 9/22
(52) U.S. Cl. ............................................................. 435/199
(58) Field of Search .............................................. 435/199

(56) References Cited

U.S. PATENT DOCUMENTS 5,200,333   4/1993   Wilson ............................... 435/172.9

OTHER PUBLICATIONS

Lunnen, et al., Gene 74:25–32 (1988).
Piekarowicz, et al., Nucleic Acids Res. 19:1831–1835 (1991).
Endow, et al., J. Mol. Biol. 112:521 (1977).
Waalwijk, et al., Nucleic Acids Res., 5:3231 (1978).
Gingeras, et al., Proc. Natl. Acad. Sci., 80:402 (1983).
Gingeras, et al., Nucleic Acids Res. 5:4105 (1978).
Sanger, et al., Proc. Natl. Acad. Sci., 74:5463 (1977).
Brown, et al., J. Mol. 140:143 (1980).

*Primary Examiner*—Charles L. Patterson, Jr.
(74) *Attorney, Agent, or Firm*—Gregory D. Williams; James Gregory Cullem

(57) ABSTRACT

In accordance with the present invention, there is provided a novel restriction endonuclease and its DNA obtainable from *Helicobacter pylori* J99 (NEB#1237), hereinafter referred to as "*Hpy*99I", which endonuclease:

(1) recognizes the nucleotide sequence 5'-CGWCG-3' in a double-stranded DNA
  (wherein G represents guanine, C represents cytosine, A represents adenine, T represents thymine and W represents either A, or T);
(2) cleaves double-stranded PhiX174 DNA to produce 8 fragments, including fragments of 3063, 629, 602, 447, 389, and 176 base pairs, and 2 fragments smaller than 100 base pairs.

3 Claims, 1 Drawing Sheet

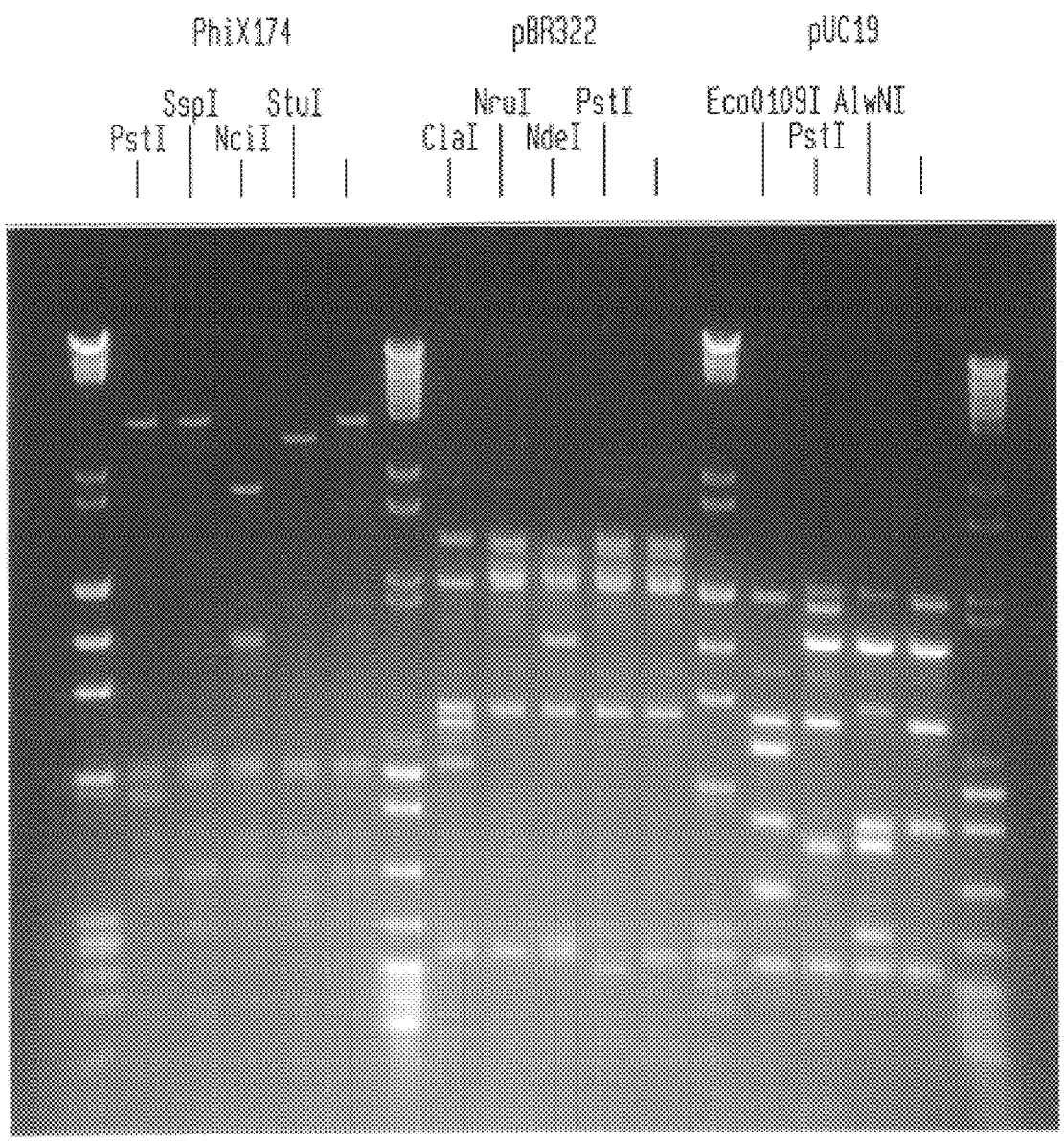

TYPE II RESTRICTION ENDONUCLEASE, HPY99I, OBTAINABLE FROM *HELICOBACTER PYLORI* J99 AND A PROCESS FOR PRODUCING THE SAME

BACKGROUND OF THE INVENTION

The present invention relates to a new Type II restriction endonuclease, Hpy99I, obtainable from *Helicobacter pylori* J99, and to the process for producing the same.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. The majority of restriction endonucleases recognize sequences of 4 to 6 nucleotides in length, although recently a small number of restriction endonucleases which recognize 7 or 8 uniquely specified nucleotides have been isolated. Most recognition sequences contain a dyad axis of symmetry and in most cases all the nucleotides are uniquely specified. However, some restriciton endonucleases have degenerate or relaxed specificities in that they recognize multiple bases at one or more positions in their recognition sequence, and some restriction endonucleases recognize asymmetric sequences. HaeIII, which recognizes the sequence 5'-GGCC-3', is an example of a restriction endonuclease having a symmetrical, non-degenerate recognition sequence, while HaeII, which recognizes 5'-(Pu)GCGC(Py)-3' typifies restriction endonucleases having a degenerate or relaxed recognition sequence. Endonucleases with symmetrical recognition sequences generally cleave symmetrically within or adjacent to the recognition site, while those that recognize asymmetric sequences tend to cleave at a distance of from 1 to 18 nucleotides away from the recognition site. More than two hundred unique restriction endonucleases have been identified among several thousands of bacterial species that have been examined to date.

Endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences 5'-(W)GGCC(W)-3 (SEQ ID NO:1)', 5'-(Pu)GCGC(Py)-3' and 5'-GGCC-3' respectively. *Escherichia coli* RY13, on the other hand, synthesizes only one enzyme, *Eco*RI, which recognizes the sequence 5'-GAATTC-3' (SEQ ID NO:2).

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecule and cleaving them in each place that the recognition sequence occurs. The disintegration that results inactivates many of the infecting genes and renders the DNA susceptible to further degradation by exonucleases.

A second component of restriction systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always modified, by virtue of the activity of its modification methylase and it is therefore insensitive to the presence of the endogenous restriction endonuclease. It is only unmodified, and therefore identifiably foreign, DNA that is sensitive to restriction endonuclease recognition and attack. More than 3000 restriction endonucleases have been isolated from various bacterial strains. Of these, more than 200 recognize unique sequences, while the rest share common recognition specificities. Restriction endonucleases which recognize the same nucleotide sequence are termed "isoschizomers." Although the recognition sequences of isoschizomers are the same, they may vary with respect to site of cleavage (e.g., XmaI v. SmaI, Endow, et al., *J. Mol. Biol.* 112:521 (1977); Waalwijk, et al., *Nucleic Acids Res.* 5:3231 (1978)) and in cleavage rate at various sites (XhoI v. PaeR7I, Gingeras, et al., *Proc. Natl. Acad. Sci.* U.S.A. 80:402 (1983)).

There is a continuing need for novel Type II restriction endonucleases. Although Type II restriction endonucleases which recognize a number of specific nucleotide sequences are currently available, new restriction endonucleases which recognize novel sequences provide greater opportunities and ability for genetic manipulation. Each new unique endonuclease enables scientists to precisely cleave DNA at new positions within the DNA molecule, with all the opportunities this offers.

SUMMARY OF THE INVENTION

In accordance with the present invention, there is provided a novel restriction endonuclease obtainable from *Helicobacter pylori* J99 (NEB#1237), hereinafter referred to as "Hpy99I", which endonuclease:

(1) recognizes the nucleotide sequence 5'-CGWCG-3' (SEQ ID NO:3) in a double-stranded DNA
   (wherein G represents guanine, C represents cytosine, A represents adenine, T represents thymine and W represents either A, or T);

(2) cleaves double-stranded PhiX174 DNA to produce 8 fragments, including fragments of 3063, 629, 602, 447, 389, and 176 base pairs, and 2 fragments smaller than 100 base pairs.

The present invention further relates to a process for the production of the novel restriction endonuclease Hpy99I. This process comprises either culturing *Helicobacter pylori* J99 under conditions suitable for expressing Hpy99I, collecting the cultured cells, obtaining a cell-free extract therefrom and separating and collecting the restriction endonuclease Hpy99I from the cell-free extract, or culturing a transformed host, such as *E. coli*, containing the genes for the Hpy99I methylase and endonuclease, collecting the cultured cells, obtaining a cell-free extract therefrom and separating and collecting the restriction endonuclease Hpy99I from the cell-free extract.

BRIEF DESCRIPTION OF THE FIGURES

FIG. 1—Agarose gel showing Hpy99I cleavage of various DNAs.

DETAILED DESCRIPTION OF THE INVENTION

The recognition sequence of the endonuclease of the present invention may be determined by mapping the locations of several Hpy99I cleavage sites in various DNAs and comparing the DNA sequences of these regions for homology, then comparing the predicted cleavage fragments of the putative recognition sequence with the observed restriction fragments produced by Hpy99I cleavage of various DNAs. The endonuclease Hpy99I was found to cleave PhiX174 DNA more than six times, producing fragments of approximately 3100, 625, 600, 450, 400, 180, along with a number of smaller fragments. The location of several cut sites were mapped to approximate positions of 1740 and 4840 (the 3100 bp fragment) and 710 and 1160 (the 450 bp fragment) by simultaneously digesting PhiX174 DNA with Hpy99I and with endonucleases which cleave at known positions, such as SspI, NciI, StuI and PstI (FIG. 1). The approximate size of several of the larger DNA fragments produced by Hpy99I digestion of PhiX174 DNA was entered into the program SITES (Gingeras, et al., *Nucl. Acids Res.* 5:4105 (1978)), which generates potential recognition sequences for the input data by comparing the fragment sizes which would result from cleavage of the DNA at any given recognition pattern with the input fragment sizes. One such potential pattern generated was 5'-CGWCG-3' (SEQ ID NO:3), which sequence occurs in PhiX174 DNA at positions consistent with the mapping data obtained, i.e. at positions 721 and 1168, and 1769 and 4832, as well as 4 other sites. The size of fragments predicted from cleavage at 5'-CGWCG-3' (SEQ ID NO:3) sites in PhiX174, pBR322, pUC19 and M13mp18 DNAs matched the observed size of fragments from cleavage of these DNAs with Hpy99I, from which we conclude that Hpy99I recognizes the sequence 5'-CGWCG-3' (SEQ ID NO:3).

The point of cleavage within the Hpy99I recognition sequence may be determined through dideoxy sequencing analysis of the terminal base sequence obtained from Hpy99I cleavage of a suitable DNA substrate (Sanger, et al., *PNAS* 74:5463–5467 (1977), Brown, et al., *J. Mol. Biol.* 140:143–148 (1980)).

In accordance with the present invention, Hpy99I is obtained by culturing *Helicobacter pylori* J99 and recovering the endonuclease from the cells. A sample of *Helicobacter pylori* J99 (NEB#1237) has been deposited under the terms and conditions of the Budapest Treaty with the American Type Culture Collection (ATCC) on Jan. 3, 2001, and received ATCC Accession No. PTA-2865.

For recovering the enzyme of the present invention *Helicobacter pylori* J99 may be grown using any suitable technique. For example, *Helicobacter pylori* J99 may be grown in Brucella broth media (BBL Microbiology Systems, Cockeysville, Md.) incubated anaerobically at 37° C. Cells in the late logarithmic stage of growth are collected by centrifugation and either disrupted immediately or stored frozen at −70° C.

The Hpy99I enzyme can be isolated from *Helicobacter pylori* J99 cells by conventional protein purification techniques. For example, cell paste is suspended in a buffer solution and treated by sonication, high pressure dispersion or enzymatic digestion to allow extraction of the endonuclease by the buffer solution. Intact cells and cellular debris are then removed by centrifugation to produce a cell-free extract containing Hpy99I. The Hpy99I endonuclease is then purified from the cell-free extract by ion-exchange chromatography, affinity chromatography, molecular sieve chromatography, or a combination of these methods to produce the endonuclease of the present invention.

The endonuclease of the present invention along with its corresponding methylase may also be obtained using recombinant DNA techniques, such as the methylation selection technique disclosed by Wilson, et al., U.S. Pat. No. 5,200,333. As an example, DNA from a bacterial strain which contains an R-M system, such as *Helicobacter pylori*, is purified, partially digested with suitable type II endonucleases, and ligated to an appropriate cleaved, dephosphorylated cloning vector. The ligated DNA is transformed into an appropriate host, such as *E. coli*, the transformants are pooled and the population of cloning vectors are purified to form libraries. The library of clones is then challenged by digesting with an endonuclease which will selectively destroy vectors which do not contain and express the methylase of the R-M system being cloned. Vectors which contain and express the methylase gene of interest will be modified at the endonuclease recognition sites of the challenging endonuclease and thus be immune from cleavage. The challenged clone pools are then transformed back into the appropriate host to recover the undigested, presumably methylase expressing clones. The transformants may be screened for endonuclease activity or cycled through further rounds of purification and selection. Finally, individual transformants are selected and their DNA purified. These clones are analyzed for resistance to cleavage by the endonuclease of interest and for common insert DNA. Cell extracts prepared from transformants which demonstrate endonuclease resistance are assayed in vitro for methyltransferase and endonuclease activities.

The present invention is further illustrated by the following Examples. These Examples are provided to aid in the understanding of the invention and are not construed as a limitation thereof.

The references cited above and below are herein incorporated by reference.

EXAMPLE I

PRODUCTION OF Epy99I ENDONUCLEASE

*Helicobacter pylori* J99 strain NEB#1237 was grown in Brucella broth media. The cells were incubated anaerobically under 5% $CO_2$ at 37° C. until late logarithmic stage. The cells were then harvested by centrifugation and stored frozen at −70° C.

3.2 grams of the cells obtained above were suspended in 20 mls buffer A (20 mM Tris-HCl, 0.1 mM EDTA, 1mM dithiothreitol, 5% glycerol, pH 7.6 at 25° C.) adjusted to 50 mM NaCl. The cell suspension was sonicated until approximately 50 mg protein per gram of cells was released. The lysate was centrifuged at 15,000 rpm for 20 minutes at 4° C. in a Beckman JA17 rotor. 21 ml of supernatant was obtained containing 120 mg of soluble protein.

The supernatant solution was applied to a 20 ml Heparin Hyper-D column (Biosepra, Marlborough, Mass.) equilibrated in buffer A adjusted to 50 mM NaCl. A 40 ml wash of buffer A adjusted to 50 mM NaCl was applied, then a 200 ml linear gradient of NaCl from 50 mM to 1M in buffer A was applied and fractions of 4 ml were collected. Fractions were assayed for Hpy99I endonuclease activity by incubation with 1 µg Lambda DNA (NEB) in 50 µl NEBuffer 4 for one hour at 37° C. Hpy99I activity eluted between 0.28M to 0.44M NaCl.

The Heparin Hyper-D column fractions containing the Hpy99I activity were pooled, diluted to 50 mM NaCl in buffer A and applied to a 3 ml Heparin-TSK column (Toso-Haas, Philadelphia, Pa.) and a 50 ml linear gradient from 0.1 M to 0.6 M NaCl in buffer A was applied to the Heparin-TSK column. The *Hpy*99I activity eluted between 0.35M to 0.4M NaCl and contained approximately 50 units of endonuclease activity. The *Hpy*99I obtained was substantially pure and free of contaminating endonuclease and exonuclease activities. Bovine serum albumin was added as a stabilizer to a final concentration of 200 µg/ml and the *Hpy*99I enzyme was dialyzed against storage buffer (50% glycerol, 50 mM NaCl, 20 mM Tris-HCl, 0.1 mM dithiothreitol, pH 7.5).

Activity Determination

*Hpy*99I activity: Samples of from 1 to 10 µl were added to 50 µl of substrate solution consisting of 1×NEBuffer 4 containing 1 µg Lambda phage DNA. The reaction was incubated at 37° C. for 60 mins. The reaction was terminated by adding 15 µl of a stop solution (50% glycerol, 50 mM EDTA pH 8.0, and 0.02% Bromophenol Blue). The reaction mixture was applied to a 1.2 % agarose gel and electrophoresed. The bands obtained were identified in comparison with DNA size standards.

Unit Definition: One unit of *Hpy*99I is defined as the amount of *Hpy*99I required to completely cleave 1.0 µg of Lambda DNA in a total reaction volume of 50 µl NEBuffer 4, supplemented with 100 µg/ml bovine serum albumin, within one hour at 37° C.

EXAMPLE II

DETERMINATION OF THE *Hpy*99I CLEAVAGE SITE

The location of *Hpy*99I cleavage relative to the recognition sequence may be determined by cleavage of a primer extension product, which is then electrophoresed alongside a set of standard dideoxy sequencing reactions produced from the same primer and template, using the method exemplified in (Sanger, et al., *PNAS* 74:5463–5467 (1977) Brown, et al., *J. Mol. Biol.* 140:143–148 (1980)). M13mp18 single-stranded DNA is typically employed as the template utilizing an *Hpy*99I recognition site located approximately 50 bp 3' to a suitable primer. For example, the sites at positions 6297 and 6310 in M13mp18 could be used with a primer complementary to M13mp18 sequence from 6355 to 6374 (5'-dGCGAAAGGGGGATGTGCTGC-3') SEQ ID NO:4). The sequencing reactions may be performed using the Sequenase version 2.0 DNA sequencing kit (Amersham Life Science) with modifications for the cleavage site determination, as exemplified in patent application Ser. No. 09/404,671. Though the position of cleavage within the *Hpy*99I had not yet been determined at time of filing, one can determine the position of cleavage using the above-referenced method.

What is claimed is:

1. A substantially pure Type II restriction endonuclease obtainable from *Helicobacter pylori* (ATCC Patent Accession No. PTA-2865) recognizing the following base sequence in double-stranded deoxyribonucleic acid molecules:

5'-CGWCG-3'
3'-GCWGC-5'.

2. A method for obtaining the Type II restriction endonuclease of claim 1, comprising cultivating a sample of *Helicobacter pylori* under conditions favoring the production of said endonuclease and separating said endonuclease therefrom.

3. The Type II restriction endonuclease of claim 1, wherein the restriction endonuclease is purified from *Helicobacter pylori* (ATCC Accession No. PTA-2865).

* * * * *

UNITED STATES PATENT AND TRADEMARK OFFICE
CERTIFICATE OF CORRECTION

PATENT NO. : 6,280,992 B1
DATED : August 28, 2001
INVENTOR(S) : Morgan et al.

It is certified that error appears in the above-identified patent and that said Letters Patent is hereby corrected as shown below:

Column 1,
Line 6, insert -- This invention was made with Government support under contract number DK53707 awarded by the National Institutes of Health. The Government has certain rights in the invention. --

Signed and Sealed this

Twenty-eighth Day of January, 2003

JAMES E. ROGAN
*Director of the United States Patent and Trademark Office*

SEQUENCE LISTING

```
<160> NUMBER OF SEQ ID NOS: 4

<210> SEQ ID NO 1
<211> LENGTH: 6
<212> TYPE: DNA
<213> ORGANISM: Haemophilus aegyptius

<400> SEQUENCE: 1 wggccw                                                                     6

<210> SEQ ID NO 2
<211> LENGTH: 6
<212> TYPE: DNA
<213> ORGANISM: Escherichia coli

<400> SEQUENCE: 2 gaattc                                                                     6

<210> SEQ ID NO 3
<211> LENGTH: 5
<212> TYPE: DNA
<213> ORGANISM: Helicobacter pylori

<400> SEQUENCE: 3 cgwcg                                                                      5

<210> SEQ ID NO 4
<211> LENGTH: 20
<212> TYPE: DNA
<213> ORGANISM: Helicobacter pylori

<400> SEQUENCE: 4
gcgaaagggg gatgtgctgc                                                     20
```